United States Patent [19]

Honda et al.

[11] Patent Number: 5,231,101
[45] Date of Patent: Jul. 27, 1993

[54] BENZO[5,6]CYCLOHEPTA[1,2-B]PYRIDINE DERIVATIVES AND ANTIALLERGIC AGENTS COMPRISING SAME

[75] Inventors: Haruyoshi Honda; Hiroyuki Mizuno, both of Chiba; Kinichi Mogi, Narita; Yoshikuni Ito, Chiba; Yasushi Kaneko, Narita; Naokata Taido, Funabashi; Susumu Sato; Tadayuki Kuraishi, both of Chiba, all of Japan

[73] Assignee: SS Pharmaceutical Co., Ltd., Tokyo, Japan

[21] Appl. No.: 821,803

[22] Filed: Jan. 17, 1992

[30] Foreign Application Priority Data

Jan. 18, 1991 [JP] Japan .................. 3-018251

[51] Int. Cl.$^5$ .......................... C07D 221/16
[52] U.S. Cl. ...................... 514/290; 546/93
[58] Field of Search .............. 546/93; 514/290

[56] References Cited

U.S. PATENT DOCUMENTS 4,282,233  8/1981  Vilani .
4,355,036 10/1982  Villani .................. 546/80

FOREIGN PATENT DOCUMENTS

WO88/03138  5/1988  PCT Int'l Appl. .
WO90/03375  4/1990  PCT Int'l Appl. .

OTHER PUBLICATIONS

Journal of Heterocyclic Chemistry, vol. 23, No. 1, Jan.-Feb., 1986, pp. 257–263, W. Halczenko, et al., "Benzocycloheptapyridines Analogs of Azatadine", (cited Apr. 27, 1992).
Halczenko, et al. *J. Heterocyclic Chemistry*, 23(1), 1986, pp. 257–263.

*Primary Examiner*—C. Warren Ivy
*Assistant Examiner*—Phyllis G. Spivack
*Attorney, Agent, or Firm*—Oblon, Spivak, McClelland, Maier & Neustadt

[57] ABSTRACT

Benzo[5,6]cyclohepta[1,2-b]pyridine derivatives of the following formula:

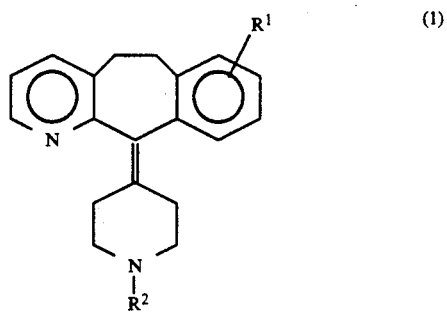

(1)

wherein $R^1$ represents a cyano, carbamoyl, alkylsulfoxy, alkylsulfonyl, tetrazolyl or sulfonic acid group, and $R^2$ represents a hydrogen atom, a cyano, phenyl, aralkyl, alkoxycarbonylalkyl, aminoalkylcarbamoylalkyl or lower alkyl group, or a group

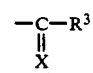

or $-X-R_4$, X being an oxygen or sulfur atom, $R^3$ standing for a hydrogen atom or a substituted or unsubstituted lower alkyl, phenyl or aralkyl group, and $R^4$ being a substituted or unsubstituted lower alkyl, phenyl or aralkyl group or an aminoalkyl group, and salts thereof. Antiallergic and antihistamic agents containing one of the above derivatives or salts as an active ingredient are also described.

3 Claims, No Drawings

BENZO[5,6]CYCLOHEPTA[1,2-B]PYRIDINE DERIVATIVES AND ANTIALLERGIC AGENTS COMPRISING SAME

BACKGROUND OF THE INVENTION

Field of the Invention

This invention relates to novel benzo[5,6]cyclohepta[1,2-b]pyridine derivatives or salts thereof and also to antiallergic agents containing same and having excellent antihistamic action and reduced central action.

Description of the Related Art

Allergic diseases such as bronchial asthma, various allergic rhinitis and Japanese cedar (Sugi) pollinosis are caused by the action of a substance released from mastocytes as a result of an allergic reaction, such as histamine on the bronchus, the nasal mucosa or the like and develop a variety of symptoms. Numerous antihistamic agents have heretofore been known as therapeutic agents for such allergic diseases, namely, antiallergic agents. Among these, azatadine, ketotifen, promethazine and the like are known as tricyclic antihistamic agents.

These antihistamic agents are, however, accompanied by the problem that they have strong central action, in other words, sedative action together with antihistamic action and, as a side effect, induce drowsiness.

In the meantime, loratadine was developed as an antihistamic agent of tricyclic system reduced in sedative action. There are also many reports on its derivatives [U.S. Pat. Nos. 3,326,924, 3,717,647, 4,282,233, 4,355,036, 4,826,853 and 4,659,716 (corresponding to Japanese Patent Application Laid-Open No. SHO 61-289087); Japanese Language Laid-Open Publication (PCT) No. HEI 2-500910, WO 88/03,138, Journal of Medicinal Chemistry 15(7), 750–754 (1972), and Arzneim.-Forsch, 36, 1311–1314 (1986)].

These compounds are, however, still not fully satisfactory as to their antihistamic action and the selectivity of the action. There is, hence, an outstanding desire for the development of a stronger antihistamic agent with reduced central action.

SUMMARY OF THE INVENTION

With the foregoing in view, the present inventors synthesized numerous benzo[5,6]cyclohepta[1,2-b]pyridine derivatives and investigated their antihistamic action and central action. As a result, it has been found that benzo[5,6]cyclohepta[1,2-b]pyridine derivatives of the below-described formula (1) and their salts have strong antihistamic action and reduced central action (sedative action), leading to the completion of this invention.

The present invention therefore provides a benzo[5,6-]cyclohepta[1,2-b]pyridine derivative of the following formula (1):

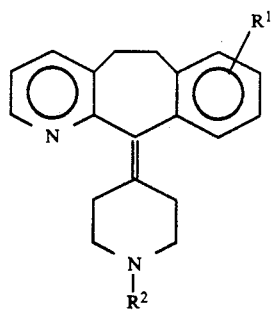

wherein $R^1$ represents a cyano, carbamoyl, alkylsulfoxy, alkylsulfonyl, tetrazolyl or sulfonic acid group; and $R^2$ represents a hydrogen atom, a cyano, phenyl, aralkyl, alkoxycarbonylalkyl, aminoalkylcarbamoylalkyl or lower alkyl group, a group

X being an oxygen or sulfur atom and $R^3$ standing for a hydrogen atom, a lower alkyl group which may be substituted by one or more halogen atoms or lower alkoxy groups, an alkylamino group, or a substituted or unsubstituted phenyl or aralkyl group, or a group —X—$R^4$, X being an oxygen or sulfur atom and $R^4$ standing for a lower alkyl group which may be substituted by one or more halogen atoms, a substituted or unsubstituted phenyl or aralkyl group, or an aminoalkyl group, or a salt thereof; and an antiallergic agent comprising the derivative or salt as an active ingredient.

The compound (1) of the present invention has strong antihistamic action and, owing to weak central action, reduced side effect, and the selectivity of its antihistamic action is extremely high. The compound (1) is, therefore, useful as an antiallergic agent. An antiallergic agent comprising the compound (1) is therefore useful for the treatment of bronchial asthma, allergic rhinitis and various pollinoses.

DETAILED DESCRIPTION OF THE INVENTION AND PREFERRED EMBODIMENTS

Examples of the alkylsulfoxy group represented by $R^1$ in the invention compound of the formula (1) include methylsulfoxy, ethylsulfoxy, n-propylsulfoxy, isopropylsulfoxy, n-butylsulfoxy, isobutylsulfoxy, n-pentylsulfoxy and n-hexylsulfoxy. On the other hand, illustrative alkylsulfonyl groups include methylsulfonyl, ethylsulfonyl, n-propylsulfonyl, isopropylsulfonyl, n-butylsulfonyl, isobutylsulfonyl, n-pentylsulfonyl and n-hexylsulfonyl. Further, examples of lower alkyl groups represented by $R^2R^3$ and $R^4$ include linear or branched alkyl groups having 1–6 carbon atoms, specifically methyl, ethyl, n-propyl, isopropyl, n-butyl, isobutyl, sec-butyl, tert-butyl, n-pentyl and n-hexyl. The halogenated alkyl group includes, for example, 2,2,2-trichloroethyl. In addition, illustrative alkoxycarbonylalkyl groups include methoxycarbonylmethyl, ethoxycarbonylmethyl, propoxycarbonylmethyl, methoxycarbonylethyl, ethoxycarbonylethyl and propoxycarbonylethyl. Exemplary aminoalkylcarbamoylalkyl groups include 2-aminoethylcarbamoylmethyl, 3- aminopropylcarbamoylmethyl, 2-aminoethylcarbamoylethyl and 3-aminopropylcarbamoylethyl.

No particular limitation is imposed on the salt of the compound (1) according to this invention insofar as the salt is pharmaceutically acceptable. Illustrative of the salt include inorganic acid salts such as hydrochloride, sulfate, nitrate and hydrobromide and organic acid salts such as acetate, oxalate, citrate, fumarate, maleate, succinate, lactate, p-toluenesulfonate and methanesulfonate.

The compound (1) of this invention can be prepared, for example, in accordance with any one of the following reaction schemes 1-6:

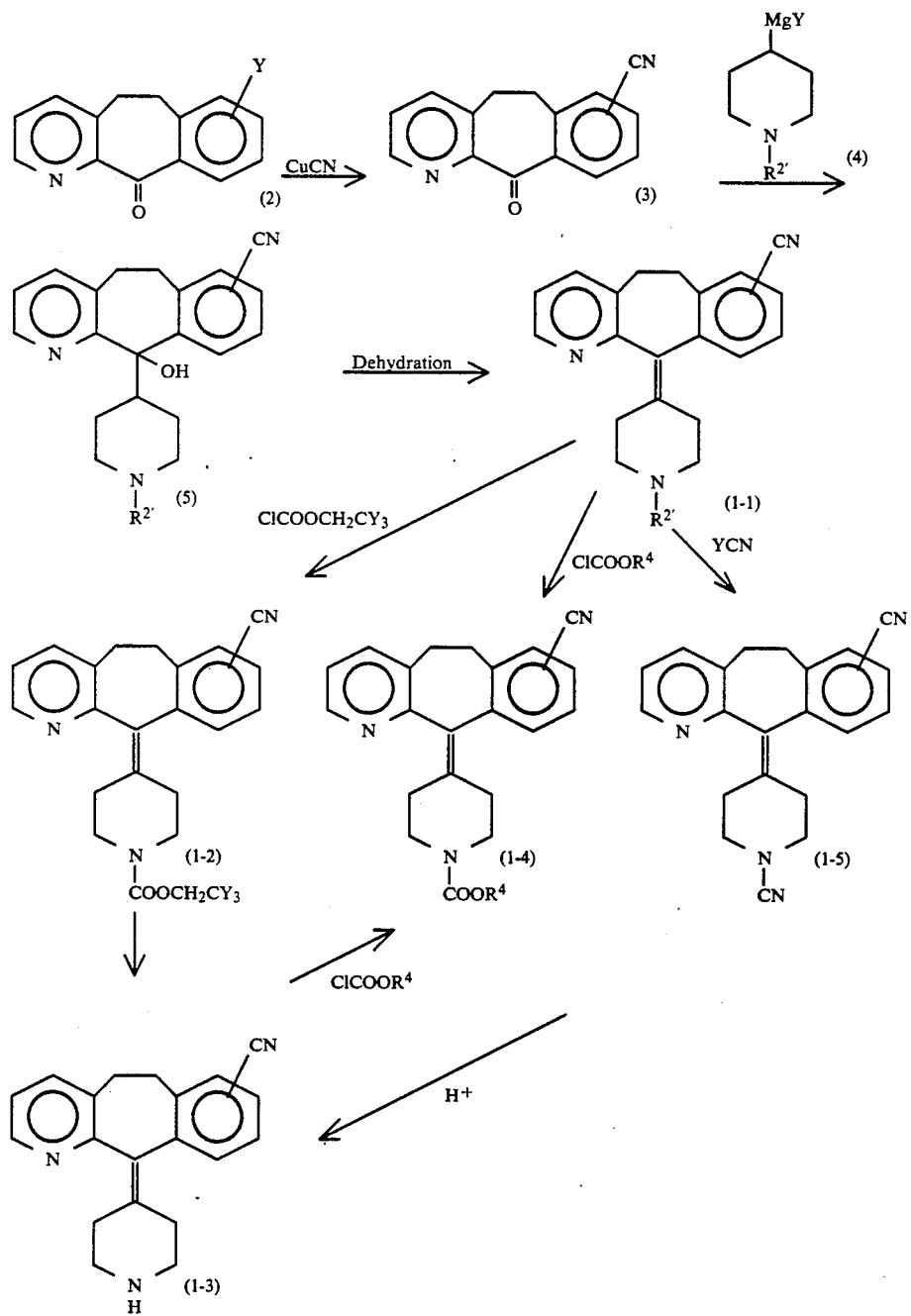

Reaction Scheme 1

-continued
Reaction Scheme 1

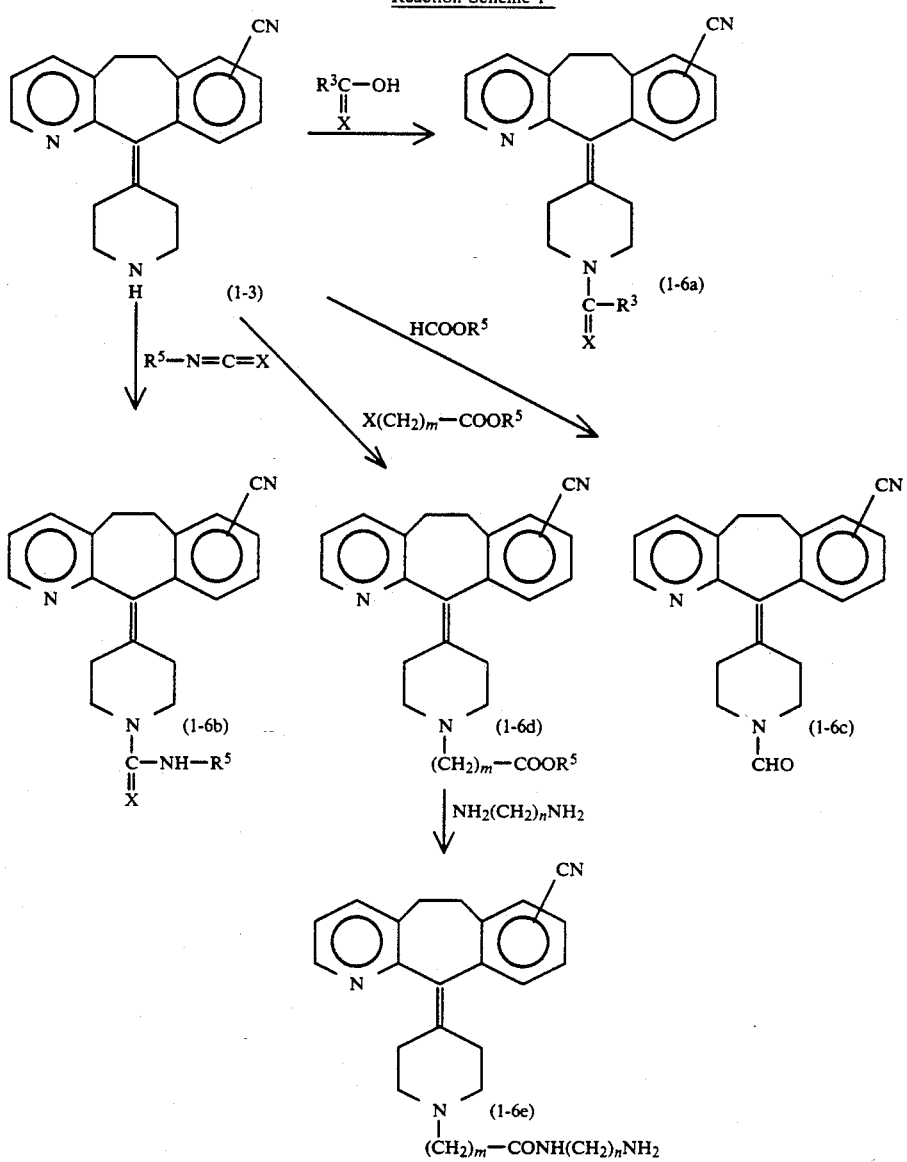

wherein Y represents a halogen atom, $R^{2'}$ means a lower alkyl, phenyl or aralkyl group, $R^5$ denotes an alkyl group, m stands for 1-6, n is 2-6, and $R^3$, $R^4$ and X have the same meaning as defined above.

Namely, a cyanating reagent such as copper cyanide is reacted with the halogeno-5,6-dihydro-1H-benzo[5,6-]cyclohepta[1,2b]pyridin-11-one (2) which has been formed, for example, by the process disclosed in U.S. Pat. No. 4,659,716 (corresponding to Japanese Patent Application Laid-Open No. SHO 61-289087), whereby the compound (3) is obtained. The Grignard reagent (4) is then reacted with the compound (3), followed by the dehydration to provide the compound (1—1) of the present invention. Further, the reaction of the compound (1—1) with the chloroformate (ClCOOCH$_2$CY$_3$ or ClCOOR$^4$) or the cyanogen halide (BrCN or the like) provides the compounds (1-2), (1-4) or (1-5). By treating the compound (1-2) with zinc/acetic acid or the like to eliminate the formate ester or hydrolyzing the compound (1-5) with an acid, the compound (1-3) can be obtained.

The reaction of the thus-obtained compound (1-3) with the carboxylic acid or thiocarboxylic acid derivative such as an acid halide or acid anhydride provides the compound (1-6a). In addition, the reaction of the compound (1-3) with the isocyanate or isothiocyanate derivative provides the compound (1-6b). The reaction of the compound (1-3) with the formate ester derivative provides the compound (1-6c). Furthermore, the reaction of the compound (1-3) with the halogenoalkylcarboxylate ester derivative provides the compound (1-6d). The reaction of the resulting compound (1-6d) with the diamine derivative provides the compound (1-6e).

In the above reactions, the Grignard reaction, hydrolysis and the like can each be conducted in a manner known per se in the art.

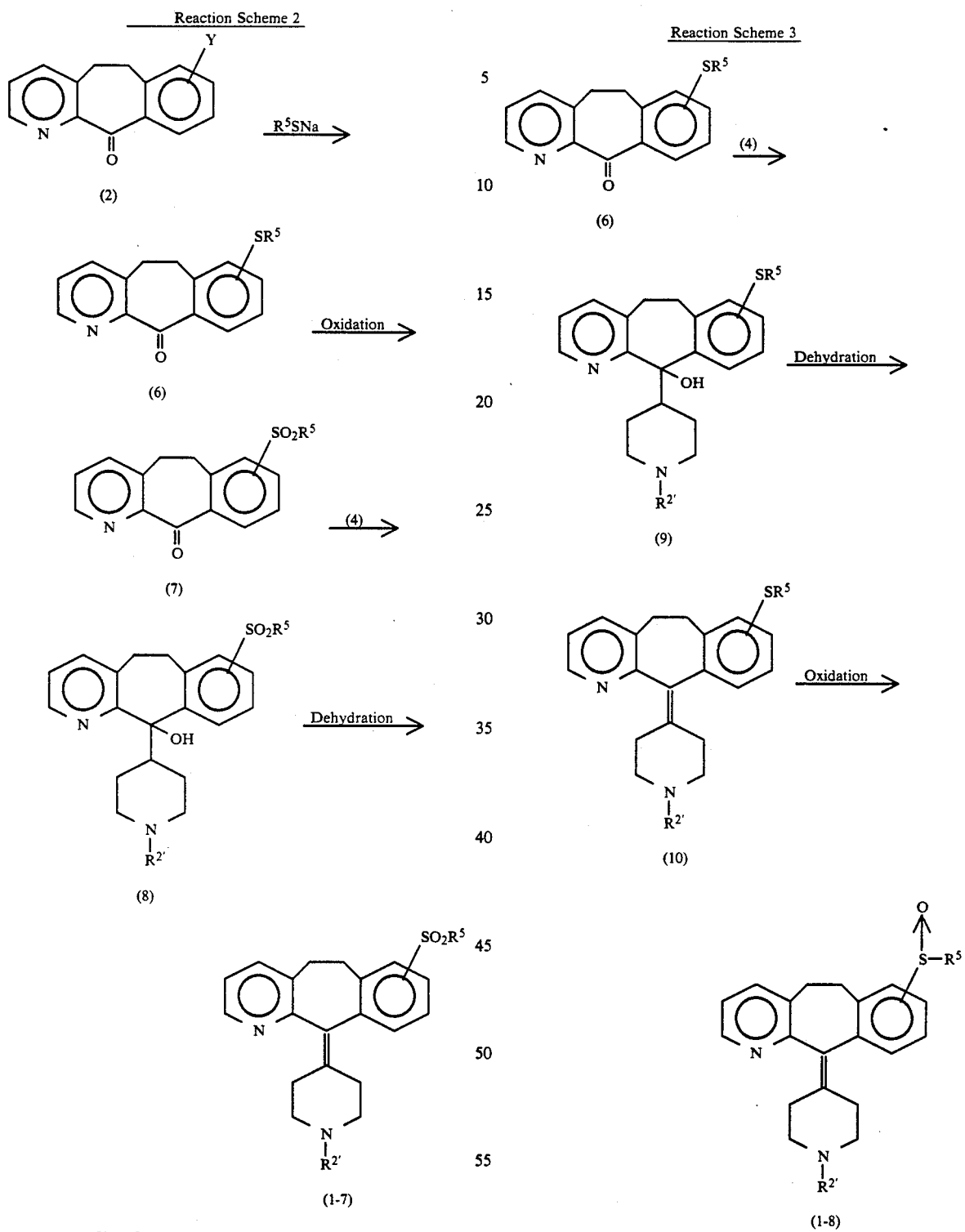

wherein $R^{2'}$, $R^5$ and Y have the same meanings as defined above.

Namely, an alkylthionating agent such as the alkyl mercaptan sodium salt is reacted with the compound (2) to obtain the compound (6). Using m-chloroperbenzoic acid, for example, the compound (6) is then oxidized into the compound (7). The Grignard reagent (4) is then reacted with the compound (7), followed by the dehydration to provide the compound (1-7) of the present invention.

wherein $R^{2'}$ and $R^5$ have the same meanings as defined above.

Namely, the Grignard reagent (4) is reacted with the compound (6), followed by the dehydration to obtain the compound (10). The compound (10) is then oxidized with an oxidizing agent such as $NaBrO_2$, whereby the compound (1-8) of this invention is obtained.

Reaction Scheme 4

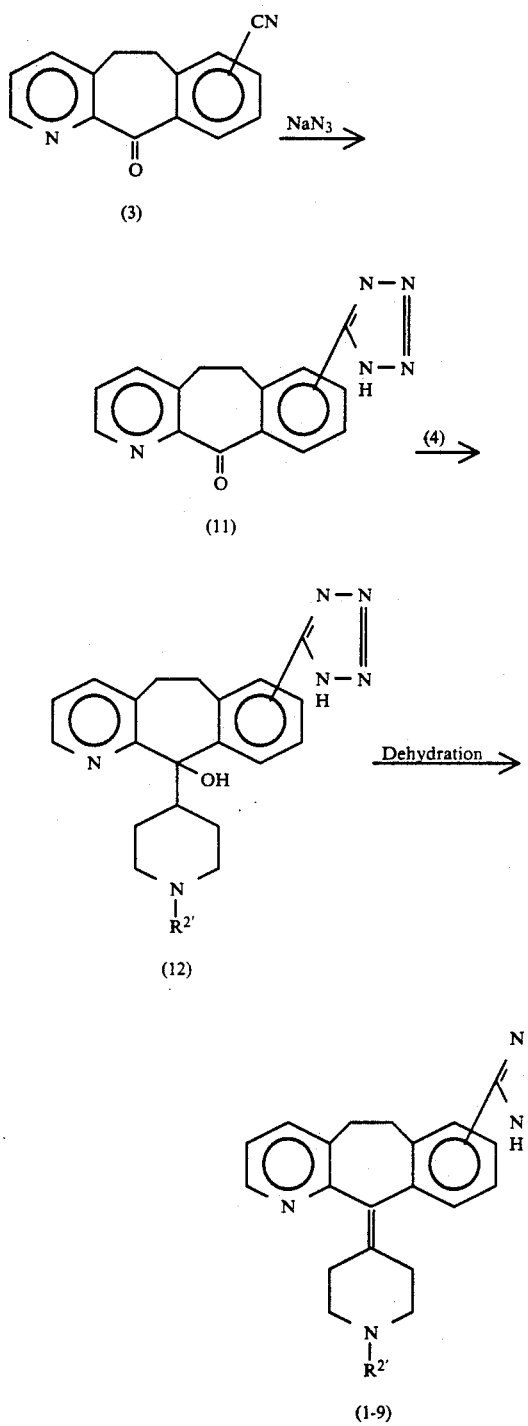

(1-9)

wherein R[2'] has the same meaning as defined above.

Namely, sodium azide or the like is reacted with the compound (3) to obtain the tetrazolyl derivative (11). The tetrazolyl derivative (11) is subjected to the Grignard reaction and then to the dehydration reaction, whereby the compound (1-9) of this invention is obtained.

Reaction Scheme 5

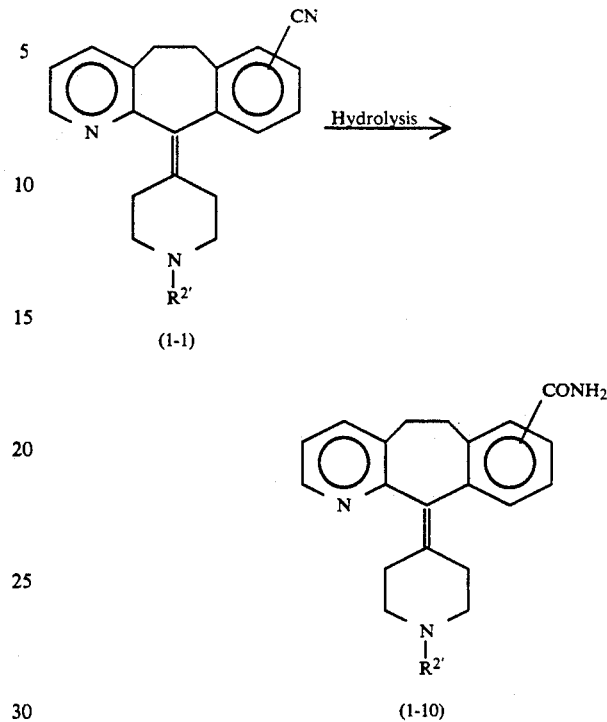

wherein R[2'] has the same meaning as defined above.

Namely, the hydrolysis of the compound (1-1) provides the compound (1-10) of this invention.

Reaction Scheme 6

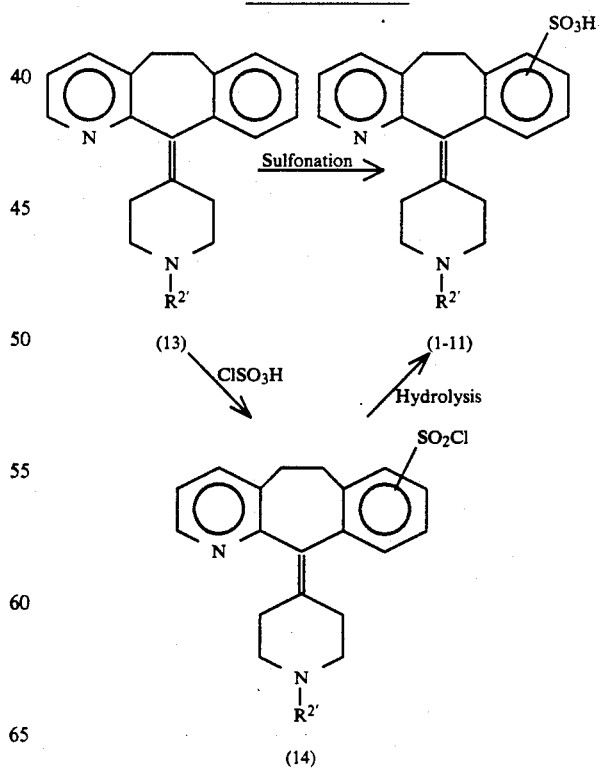

wherein R[2'] has the same meaning as defined above.

Namely, fuming sulfuric acid is reacted with 11-(1-methyl-4-piperidylidene)-6,11-dihydro-5H-benzo[5,6]-cyclohepta[1,2-b]pyridine (13) obtained in accordance with the process disclosed, for example, in Journal of Medicinal Chemistry, 15, 750–754 (1972) or chlorosulfonic acid is reacted with the compound (13) to obtain the compound (14) followed by the hydrolysis, so that the compound (1-11) of the present invention is obtained.

In each of the compounds (1-7), (1-8), (1-9), (1-10) and (1-11) described, the N-substituting group of the piperidino group can be changed as in Reaction Scheme 1.

Specific examples of the invention compounds (1) include the following compounds:

8-Cyano-11-(1-methyl-4-piperidylidene)-6,11-dihydro-5H-benzo[5,6]cyclohepta[1,2-b]pyridine;
8-Cyano-11-(1-phenyl-4-piperidylidene)-6,11-dihydro-5H-benzo[5,6]cyclohepta[1,2-b]pyridine;
11-(1-Methyl-4-piperidylidene)-6,11-dihydro-5H-benzo[5,6]cyclohepta[1,2-b]pyridine-8-carboxamide;
11-(1-Phenyl-4-piperidylidene)-6,11-dihydro-5H-benzo[5,6]cyclohepta[1,2-b]pyridine-8-carboxamide;
8-Cyano-11-(1-ethoxycarbonyl-4-piperidylidene)-6,11-dihydro-5H-benzo[5,6]cyclohepta[1,2-b]pyridine;
8-Cyano-11-(4-piperidylidene)-6,11-dihydro-5H-benzo[5,6]cyclohepta[1,2-b]pyridine;
8-Cyano-11-(1-acetyl-4-piperidylidene)-6,11-dihydro-5H-benzo[5,6]cyclohepta[1,2-b]pyridine;
8-Cyano-11-(1-benzoyl-4-piperidylidene)-6,11-dihydro-5H-benzo[5,6]cyclohepta[1,2-b]pyridine;
8-Cyano-11-(1-cinnamoyl-4-piperidylidene)-6,11-dihydro-5H-benzo[5,6]cyclohepta[1,2-b]pyridine;
8-Cyano-11-(1-benzyloxycarbonyl-4-piperidylidene)-6,11-dihydro-5H-benzo[5,6]cyclohepta[1,2-b]pyridine;
8-Cyano-11-(1-thioacetyl-4-piperidylidene)-6,11-dihydro- 5H-benzo[5,6]cyclohepta[1,2-b]pyridine;
8-Cyano-11-(1-thiobenzoyl-4-piperidylidene)-6,11-dihydro-5H-benzo[5,6]cyclohepta[1,2-b]pyridine;
8-Cyano-11-(1-thioethoxycarbonyl-4-piperidylidene)-6,11-dihydro-5H-benzo[5,6]cyclohepta[1,2-b]pyridine;
8-Cyano-11-(1-methylaminocarbonyl-4-piperidylidene)-6,11-dihydro-5H-benzo[5,6]cyclohepta[1,2-b]pyridine;
8-Cyano-11-(1-methylamionothiocarbonyl-4-piperidylidene)-6,11-dihydro-5H-benzo[5,6]cyclohepta[1,2-b]pyridine;
8-Cyano-11-[1-(2,2,2-trichloroethoxycarbonyl)-4-piperidylidene)-6,11-dihydro-5H-benzo[5,6]cyclohepta[1,2-b]pyridine;
8-Methylsulfoxy-11-(1-methyl-4-piperidylidene)-6,11-dihydro-5H-benzo[5,6]cyclohepta[1,2-b]pyridine;
8-Methylsulfoxy-11-(1-phenyl-4-piperidylidene)-6,11-dihydro-5H-benzo[5,6]cyclohepta[1,2-b]pyridine;
8-Methylsulfoxy-11-(4-piperidylidene)-6,11-dihydro-5H-benzo[5,6]cyclohepta[1,2-b]pyridine;
8-Methylsulfoxy-11-(1-acetyl-4-piperidylidene)6,11-dihydro-5H-benzo[5,6]cyclohepta[1,2-b]pyridine;
8-Methylsulfoxy-11-(1-benzoyl-4-piperidylidene)-6,11-dihydro-5H-benzo[5,6]cyclohepta[1,2-b]pyridine;
8-Methylsulfoxy-11-(1-cinnamoyl-4-piperidylidene)-6,11-dihydro-5H-benzo[5,6]cyclohepta[1,2-b]pyridine;
8-Methylsulfoxy-11-(1-benzyloxycarbonyl-4-piperidylidene)-6,11-dihydro-5H-benzo[5,6]cyclohepta[1,2-b]pyridine;
8-Methylsulfoxy-11-(1-thioacetyl-4-piperidylidene)-6,11-dihydro-5H-benzo[5,6]cyclohepta[1,2-b]pyridine;
8-Methylsulfoxy-11-(1-thiobenzoyl-4-piperidylidene)-6,11-dihydro-5H-benzo[5,6]cyclohepta[1,2-b]pyridine;
8-Methylsulfoxy-11-(1-thioethoxycarbonyl-4-piperidylidene)-6,11-dihydro-5H-benzo[5,6]cyclohepta[1,2-b]pyridine;
8-Methylsulfoxy-11-(1-methylaminocarbonyl-4-piperidylidene)-6,11-dihydro-5H-benzo[5,6]cyclohepta[1,2-b]pyridine;
11-[1-(1,1,1-trichloroethoxycarbonyl)-4-piperidylidene)-6,11-dihydro-5H-benzo[5,6]cyclohepta[1,2-b]pyridine;
11-(1-Methyl-4-piperidylidene)-6,11-dihydro-5H-benzo[5,6]cyclohepta[1,2-b]pyridine-8-tetrazole;
11-(1-Phenyl-4-piperidylidene)-6,11-dihydro-5H-benzo[5,6]cyclohepta[1,2-b]pyridine-8-tetrazole;
11-(4-piperidylidene)-6,11-dihydro-5H-benzo[5,6]1,2-b]pyridine-8-tetrazole;
11-(1-Ethoxycarbonyl-4-piperidylidene)-6,11-dihydro-5H-benzo[5,6]cyclohepta[1,2-b]pyridine-8-tetrazole;
11-(1-Acetyl-4-piperidylidene)-6,11-dihydro-5H-benzo[5,6]cyclohepta[1,2-b]pyridine-8-tetrazole;
11-(1-Benzoyl-4-piperidylidene)-6,11-dihydro-5H-benzo[5,6]cyclohepta[1,2-b]pyridine-8-tetrazole;
11-(1-Cinnamoyl-4-piperidylidene)-6,11-dihydro-5H-benzo[5,6]cyclohepta[1,2-b]pyridine-8-tetrazole;
11-(1-Benzyloxycarbonyl-4-piperidylidene)-6,11-dihydro-5H-benzo[5,6]cyclohepta[1,2-b]pyridine-8-tetrazole;
11-(1-Thioacetyl-4-piperidylidene)-6,11-dihydro-5H-benzo[5,6]cyclohepta[1,2-b]pyridine-8-tetrazole;
11-(1-Thiobenzoyl-4-piperidylidene)-6,11-dihydro-5H-benzo[5,6]cyclohepta[1,2-b]pyridine-8-tetrazole;
11-(1-Thioethoxycarbonyl-4-piperidylidene)-6,11-dihydro-5H-benzo[5,6]cyclohepta[1,2-b]pyridine-8-tetrazole;
11-(1-Methylaminocarbonyl-4-piperidylidene)-6,11-dihydro-5H-benzo[5,6]cyclohepta[1,2-b]pyridine-8tetrazole;
11-(1-Methylaminothiocarbonyl-4-piperidylidene)-6,11-dihydro-5H-benzo[5,6]cyclohepta[1,2-b]-pyridine-8-tetrazole;
11-[1-(1,1,1-trichloroethoxycarbonyl)-4-piperidylidene]-6,11-dihydro-5H-benzo[5,6]cyclohepta[1,2-b]pyridine-8-tetrazole;
11-(1-Ethoxycarbonyl-4-piperidylidene)-6,11-dihydro-5H-benzo[5,6]cyclohepta[1,2-b]pyridine-8carboxamide;
11-(4-Piperidylidene)-6,11-dihydro-5H-benzo[5,6]cyclohepta[1,2-b]pyridine-8-carboxamide;
11-(1-Acetyl-4-piperidylidene)-6,11-dihydro-5H-benzo[5,6]cyclohepta[1,2-b]pyridine-8-carboxamide;
11-(1-Benzoyl-4-piperidylidene)-6,11-dihydro-5H-benzo[5,6]cyclohepta[1,2-b]pyridine-8-carboxamide;
11-(1-Cinnamoyl-4-piperidylidene)-6,11-dihydro-5H-benzo[5,6]cyclohepta[1,2-b]pyridine-8-carboxamide;
11-(1-Benzyloxycarbonyl-4-piperidylidene)-6,11-dihydro-5H-benzo[5,6]cyclohepta[1,2-b]pyridine-8carboxamide;
11-(1-Thioacetyl-4-piperidylidene)-6,11-dihydro-5H-benzo[5,6]cyclohepta[1,2-b]pyridine-8-carboxamide;
11-(1-Thiobenzoyl-4-piperidylidene)-6,11-dihydro-5H-benzo[5,6]cyclohepta[1,2-b]pyridine-8-carboxamide;

11-(1-Thioethoxycarbonyl-4-piperidylidene)-6,11-dihydro-5H-benzo[5,6]cyclohepta[1,2-b]pyridine-8carboxamide;

11-(1-Methylaminocarbonyl-4-piperidylidene)-6,11-dihydro-5H-benzo[5,6]cyclohepta[1,2-b]pyridine-8carboxamide;

11-(1-Methylaminothiocarbonyl-4-piperidylidene)-6,11-dihydro-5H-benzo[5,6]cyclohepta[1,2-b]pyridine-8-carboxamide;

11-[1-(1,1,1-trichloroethoxycarbonyl)-4-piperidylidene]-6,11-dihydro-5H-benzo[5,6]cyclohepta[1,2-b]pyridine-8-carboxamide;

11-(1-Methyl-4-piperidylidene)-6,11-dihydro-5H-benzo[5,6]cyclohepta[1,2-b]pyridine-8-sulfonic acid;

11-(1-Phenyl-4-piperidylidene)-6,11-dihydro-5H-benzo[5,6]cyclohepta[1,2-b]pyridine-8-sulfonic acid;

11-(1-Ethoxycarbonyl-4-piperidylidene)-6,11-dihydro-5H-benzo[5,6]cyclohepta[1,2-b]pyridine-8-sulfonic acid;

11-(4-Piperidylidene)-6,11-dihydro-5H-benzo[5,6]-cyclohepta[1,2-b]pyridine-8-sulfonic acid;

11-(1-Acetyl-4-piperidylidene)-6,11-dihydro-5H-benzo[5,6]cyclohepta[1,2-b]pyridine-8-sulfonic acid;

11-(1-Benzoyl-4-piperidylidene)-6,11-dihydro-5H-benzo[5,6]cyclohepta[1,2-b]pyridine-8-sulfonic acid;

11-(1-Cinnamoyl-4-piperidylidene)-6,11-dihydro-5H-benzo[5,6]cyclohepta[1,2-b]pyridine-8-sulfonic acid;

11-(1-Benzoyloxycarbonyl-4-piperidylidene)-6,11-dihydro-5H-benzo[5,6]cyclohepta[1,2-b]pyridine-8sulfonic acid;

11-(1-Thioacetyl-4-piperidylidene)-6,11-dihydro-5H-benzo[5,6]cyclohepta[1,2-b]pyridine-8-sulfonic acid;

11-(1-Thiobenzoyl-4-piperidylidene)-6,11-dihydro-5H-benzo[5,6]cyclohepta[1,2-b]pyridine-8-sulfonic acid;

11-(1-Thioethoxycarbonyl-4-piperidylidene)-6,11-dihydro-5H-benzo[5,6]cyclohepta[1,2-b]pyridine-8sulfonic acid;

11-(1-Methylaminocarbonyl-4-piperidylidene)-6,11-dihydro-5H-benzo[5,6]cyclohepta[1,2-b]pyridine-8sulfonic acid;

11-(1-Methylaminothiocarbonyl-4-piperidylidene)-6,11-dihydro-5H-benzo[5,6]cyclohepta[1,2-b]pyridine-8-sulfonic acid;

11-[1-(1,1,1-trichloroethoxycarbonyl)-4-piperidylidene]6,11-dihydro-5H-benzo[5,6]cyclohepta[1,2-b]pyridine-8-sulfonic acid;

8-Methylsulfonyl-11-(1-methyl-4-piperidylidene)-6,11-dihydro-5H-benzo[5,6]cyclohepta[1,2-b]pyridine;

8-Methylsulfonyl-11-(1-phenyl-4-piperidylidene)-6,11-dihydro-5H-benzo[5,6]cyclohepta[1,2-b]pyridine;

8-Methylsulfonyl-11-(1-ethoxycarbonyl-4-piperidylidene)-6,11-dihydro-5H-benzo[5,6]cyclohepta[1,2-b]pyridine;

8-Methylsulfonyl-11-(4-piperidylidene)-6,11-dihydro-5H-benzo[5,6]cyclohepta[1,2-b]pyridine;

8-Methylsulfonyl-11-(1-acetyl-4-piperidylidene)-6,11-dihydro-5H-benzo[5,6]cyclohepta[1,2-b]pyridine;

8-Methylsulfonyl-11-(1-benzoyl-4-piperidylidene)-6,11-dihydro-5H-benzo[5,6]cyclohepta[1,2-b]pyridine;

8-Methylsulfonyl-11-(1-cinnamoyl-4-piperidylidene)-6,11-dihydro-5H-benzo[5,6]cyclohepta[1,2-b]pyridine;

8-Methylsulfonyl-11-(1-benzyloxycarbonyl-4-piperidylidene)-6,11-dihydro-5H-benzo[5,6]cyclohepta[1,2-b]pyridine;

8-Methylsulfonyl-11-(1-thioacetyl-4-piperidylidene)-6,11-dihydro-5H-benzo[5,6]cyclohepta[1,2-b]pyridine;

8-Methylsulfonyl-11-(1-thiobenzoyl-4-piperidylidene)-6,11-dihydro-5H-benzo[5,6]cyclohepta[1,2-b]pyridine;

8-Methylsulfonyl-11-(1-thioethoxycarbonyl-4-piperidylidene)-6,11-dihydro-5H-benzo[5,6]cyclohepta[1,2-b]pyridine;

8-Methylsulfonyl-11-(1-methylaminocarbonyl-4-piperidylidene)-6,11-dihydro-5H-benzo[5,6]cyclohepta[1,2-b]pyridine;

8-Methylsulfonyl-11-(1-methylaminothiocarbonyl-4-piperidylidene)-6,11-dihydro-5H-benzo[5,6]cyclohepta[1,2-b]pyridine;

8-Methylsulfonyl-11-[1-(1,1,1-trichloroethoxycarbonyl)-4-piperidylidene)-6,11-dihydro-5H-benzo[5,6]cyclohepta[1,2-b]pyridine;

8-Cyano-11-(1-ethyl-4-piperidylidene)-6,11-dihydro-5H-benzo[5,6]cyclohepta[1,2-b]pyridine;

8-Cyano-11-(1-butyl-4-piperidylidene)-6,11-dihydro-5H-benzo[5,6]cyclohepta[1,2-b]pyridine;

8-Cyano-11-(1-benzyl-4-piperidylidene)-6,11-dihydro-5H-benzo[5,6]cyclohepta[1,2-b]pyridine;

8-Cyano-11-(1-propionyl-4-piperidylidene)-6,11-dihydro-5H-benzo[5,6]cyclohepta[1,2-b]pyridine;

8-Cyano-11-(1-butyroyl-4-piperidylidene)-6,11-dihydro-5H-benzo[5,6]cyclohepta[1,2-b]pyridine;

8-Cyano-11-[1-(3-chlorophenylacetyl)-4-piperidylidene]-6,11-dihydro-5H-benzo[5,6]cyclohepta[1,2-b]pyridine;

8-Cyano-11-[1-(3,4-dimethoxybenzoyl)-4-piperidylidene]-6,11-dihydro-5H-benzo[5,6]cyclohepta[1,2-b]pyridine;

8-Cyano-11-(1-methoxyacetyl-4piperidylidene)-6,11-dihydro-5H-benzo[5,6]cyclohepta[1,2-b]-pyridine;

8-Cyano-11-(1-aminoacetyl-4-piperidylidene)-6,11-dihydro-5H-benzo[5,6]cyclohepta[1,2-b]pyridine;

11-(1-Ethyl-4-piperidylidene)-6,11-dihydro-5H-benzo[5,6]cyclohepta[1,2-b]pyridine-8-carboxamide;

11-(1-Butyl-4-piperidylidene)-6,11-dihydro-5H-benzo[5,6]cyclohepta[1,2-b]pyridine-8-carboxamide;

11-(1-Benzyl-4-piperidylidene)-6,11-dihydro-5H-benzo[5,6]cyclohepta[1,2-b]pyridine-8-carboxamide;

11-(1-Propionyl-4-piperidylidene)-6,11-dihydro-5H-benzo[5,6]cyclohepta[1,2-b]pyridine-8-carboxamide;

11-(1-Butyroyl-4-piperidylidene)-6,11-dihydro-5H-benzo[5,6]cyclohepta[1,2-b]pyridine-8-carboxamide;

11-[1-(3-chlorophenylacetyl)-4-piperidylidene]-6,11-dihydro-5H-benzo[5,6]cyclohepta[1,2-b]pyridine-8-carboxamide;

11-[1-(3,4-dimethoxybenzoyl)-4-piperidylidene]-6,11-dihydro-5H-benzo[5,6]cyclohepta[1,2-b]pyridine-8-carboxamide;

11-(1-Methoxyacetyl-4-piperidylidene)-6,11-dihydro-5H-benzo[5,6]cyclohepta[1,2-b]pyridine-8carboxamide;

11-(1-Aminoacetyl-4-piperidylidene)-6,11-dihydro-5H-benzo[5,6]cyclohepta[1,2-b]pyridine-8-carboxamide;

8-Methylsulfoxy-11-(1-ethyl-4-piperidylidene)6,11-dihydro-5H-benzo[5,6]cyclohepta[1,2-b]pyridine;

8-Methylsulfoxy-11-(1-butyl-4-piperidylidene)6,11-dihydro-5H-benzo[5,6]cyclohepta[1,2-b]pyridine;

8-Methylsulfoxy-11-(1-benzyl-4-piperidylidene)-6,11-dihydro-5H-benzo[5,6]cyclohepta[1,2-b]pyridine;

8-Methylsulfoxy-11-(1-propionyl-4-piperidylidene)-6,11-dihydro-5H-benzo[5,6]cyclohepta[1,2-b]pyridine;

8-Methylsulfoxy-11-(1-butyroyl-4-piperidylidene)-6,11-dihydro-5H-benzo[5,6]cyclohepta[1,2-b]pyridine;

8-Methylsulfoxy-11-[1-(3-chlorophenylacetyl)-4-piperidylidene]-6,11-dihydro-5H-benzo[5,6]cyclohepta[1,2-b]pyridine;

8-Methylsulfoxy-11-[1-(3,4-dimethoxybenzoyl)-4-piperidylidene]-6,11-dihydro-5H-benzo[5,6]cyclohepta[1,2-b]pyridine;

8-Methylsulfoxy-11-(1-methoxyacetyl-4-piperidylidene)-6,11-dihydro-5H-benzo[5,6]cyclohepta[1,2-b]pyridine;

8-Methylsulfoxy-11-(1-aminoacetyl-4-piperidylidene)-6,11-dihydro-5H-benzo[5,6]cyclohepta[1,2b]pyridine;

8-Propylsulfoxy-11-(1-ethyl-4-piperidylidene)-6,11-dihydro-5H-benzo[5,6]cyclohepta[1,2-b]pyridine;

8-Propylsulfoxy-11-(1-butyl-4-piperidylidene)-6,11-dihydro-5H-benzo[5,6]cyclohepta[1,2-b]pyridine;

8-Propylsulfoxy-11-(1-benzyl-4-piperidylidene)-6,11-dihydro-5H-benzo[5,6]cyclohepta[1,2-b]pyridine;

8-Propylsulfoxy-11-(1-propionyl-4-piperidylidene)-6,11-dihydro-5H-benzo[5,6]cyclohepta[1,2-b]pyridine;

8-Propylsulfoxy-11-(1-butyroyl-4-piperidylidene)-6,11-dihydro-5H-benzo[5,6]cyclohepta[1,2-b]pyridine;

8-Propylsulfoxy-11-[1-(3-chlorophenylacetyl)-4-piperidylidene]-6,11-dihydro-5H-benzo[5,6]cyclohepta[1,2-b]pyridine;

8-Propylsulfoxy-11-[1-(3-dimethoxybenzoyl)-4-piperidylidene]-6,11-dihydro-5H-benzo[5,6]cyclohepta[1,2-b]pyridine;

8-Propylsulfoxy-11-(1-methoxyacetyl-4-piperidylidene)-6,11-dihydro-5H-benzo[5,6]cyclohepta[1,2-b]pyridine;

8-Propylsulfoxy-11(1-aminoacetyl-4-piperidylidene)-6,11-dihydro-5H-benzo[5,6]cyclohepta[1,2-b]pyridine;

8-Methylsulfonyl-11-(1-ethyl-4-piperidylidene)-6,11-dihydro-5H-benzo[5,6]cyclohepta[1,2-b]pyridine;

8-Methylsulfonyl-11(1-butyl-4-piperidylidene)-6,11-dihydro-5H-benzo[5,6]cyclohepta[1,2-b]pyridine;

8-Methylsulfonyl-11-(1-benzyl-4-piperidylidene)-6,11-dihydro-5H-benzo[5,6]cyclohepta[1,2-b]pyridine;

8-Methylsulfonyl-11-(1-propionyl-4-piperidylidene)-6,11-dihydro-5H-benzo[5,6]cyclohepta[1,2-b]pyridine;

8-Methylsulfonyl-11-(1-butyroyl-4-piperidylidene)-6,11-dihydro-5H-benzo[5,6]cyclohepta[1,2b]pyridine;

8-Methylsulfonyl-11-[1-(3-chlorophenylacetyl)-4-piperidylidene]-6,11-dihydro-5H-benzo[5,6]cyclohepta[1,2-b]pyridine;

8-Methylsulfonyl-11-[1-(3,4-dimethoxybenzoyl)-4-piperidylidene]-6,11-dihydro-5H-benzo[5,6]cyclohepta[1,2-b]pyridine;

8-Methylsulfonyl-11-(1-methoxyacetyl-4-piperidylidene)-6,11-dihydro-5H-benzo[5,6]cyclohepta[1,2-b]pyridine;

8-Methylsulfonyl-11-(1-aminoacetyl-4-piperidylidene)-6,11-dihydro-5H-benzo[5,6]cyclohepta[1,2-b]pyridine;

8-Propylsulfonyl-11-(1-ethyl-4-piperidylidene)-6,11-dihydro-5H-benzo[5,6]cyclohepta[1,2-b]pyridine;

8-Propylsulfonyl-11-(1-butyl-4-piperidylidene)-6,11-dihydro-5H-benzo[5,6]cyclohepta[1,2-b]pyridine;

8-Propylsulfonyl-11-(1-benzyl-4-piperidylidene)6,11-dihydro-5H-benzo[5,6]cyclohepta[1,2-b]pyridine;

8-Propylsulfonyl-11-(1-propionyl-4-piperidylidene)-6,11-dihydro-5H-benzo[5,6]cyclohepta[1,2b]pyridine;

8-Propylsulfonyl-11-(1-butyroyl-4-piperidylidene)-6,11-dihydro-5H-benzo[5,6]cyclohepta[1,2b]pyridine;

8-Propylsulfonyl-11-[1-(3-chlorophenylacetyl)-4-piperidylidene]-6,11-dihydro-5H-benzo[5,6]cyclohepta[1,2-b]pyridine;

8-Propylsulfonyl-11-[1-(3,4-dimethoxybenzoyl)-4-piperidylidene]-6,11-dihydro-5H-benzo[5,6]cyclohepta[1,2-b]pyridine;

8-Propylsulfonyl-11-(1l-methoxyacetyl-4-piperidylidene)-6,11-dihydro-5H-benzo[5,6]cyclohepta[1,2-b]pyridine;

8-Propylsulfonyl-11-(1-aminoacetyl-4-piperidylidene)-6,11-dihydro-5H-benzo[5,6]cyclohepta[1,2b]pyridine;

11-(1-Ethyl-4-piperidylidene)-6,11-dihydro-5H-benzo[5,6]cyclohepta[1,2-b]pyridine-8-sulfonic acid;

11-(1-Butyl-4-piperidylidene)-6,11-dihydro-5H-benzo[5,6]cyclohepta[1,2-b]pyridine-8-sulfonic acid;

11-(1-Benzyl-4-piperidylidene) -5H-benzo[5,6]cyclohepta[1,2-b]pyridine-8-sulfonic acid;

11-(1-Propionyl-4-piperidylidene)-6,11-dihydro-5H-benzo[5,6]cyclohepta[1,2-b]pyridine-8-sulfonic acid;

11-(1-Butyroyl-4-piperidylidene)-6,11-dihydro-5H-benzo[5,6]cyclohepta[1,2-b]pyridine-8-sulfonic acid;

11-[1-(3-chlorophenylacetyl)-4-piperidylidene)-6,11-dihydro-5H-benzo[5,6]cyclohepta[1,2-b]pyridine-8-sulfonic acid;

11-[1-(3,4-dimethoxybenzoyl)-4-piperidylidene)-6,11-dihydro-5H-benzo[5,6]cyclohepta[1,2-b]pyridine-8-sulfonic acid;

11-(1-Methoxyacetyl-4-piperidylidene)-6,11-dihydro-5H-benzo[5,6]cyclohepta[1,2-b]pyridine-8sulfonic acid;

11-(1-Aminoacetyl-4-piperidylidene)-6,11-dihydro-5H-benzo[5,6]cyclohepta[1,2-b]pyridine-8-sulfonic acid;

11-(1-Ethyl-4-piperidylidene)-6,11-dihydro-5H-benzo[5,6]cyclohepta[1,2-b]pyridine-8-tetrazole;

11-(1-Butyl-4-piperidylidene)-6,11-dihydro-5H-benzo[5,6]cyclohepta[1,2-b]pyridine-8-tetrazole;

11-(1-Benzyl-4-piperidylidene)-6,11-dihydro-5H-benzo[5,6]cyclohepta[1,2-b]pyridine-8-tetrazole;

11-(1-Propionyl-4-piperidylidene)-6,11-dihydro-5H-benzo[5,6]cyclohepta[1,2-b]pyridine-8-tetrazole;

11-(1-Butyroyl-4-piperidylidene)-6,11-dihydro-5H-benzo[5,6]cyclohepta[1,2-b]pyridine-8-tetrazole;

11-[1-(3-chlorophenylacetyl)-4-piperidylidene]-6,11-dihydro-5H-benzo[5,6]cyclohepta[1,2-b]pyridine-8-tetrazole;

11-[1-(3,4-dimethoxybenzoyl)-4-piperidylidene]-6,11-dihydro-5H-benzo[5,6]cyclohepta[1,2-b]pyridine-8-tetrazole;

11-(1-Methoxyacetyl-4-piperidylidene)-6,11-dihydro-5H-benzo[5,6]cyclohepta[1,2-b]pyridine-8tetrazole;

1-(1-Aminoacetyl-4-piperidylidene)-6,11-dihydro-5H-benzo[5,6]cyclohepta[1,2-b]pyridine-8-tetrazole;

8-Cyano-11-(1-cyano-4-piperidylidene)-6,11-dihydro-5H-benzo[5,6]cyclohepta[1,2-b]pyridine;

8-Methylsulfoxy-11-(1-cyano-4-piperidylidene)-6,11-dihydro-5H-benzo[5,6]cyclohepta[1,2-b]pyridine;

8-Methylsulfonyl-11-(1-cyano-4-piperidylidene)-6,11-dihydro-5H-benzo[5,6]cyclohepta[1,2-b]pyridine;

8-Cyano-11-(1-formyl-4-piperidylidene)-6,11-dihydro-5H-benzo[5,6]cyclohepta[1,2-b]pyridine;

8-Methylsulfoxy-(1-formyl-4-piperidylidene)-6,11-dihydro-5H-benzo[5,6]cyclohepta[1,2-b]pyridine;

8-Methylsulfonyl-11-(1-cyano-4-piperidylidene)-6,11-dihydro-5H-benzo[5,6]cyclohepta[1,2-b]pyridine;

8-Cyano-11-(1-methoxycarbonylmethyl-4-piperidylidene)-6,11-dihydro-5H-benzo[5,6]cyclohepta[1,2b]pyridine;

8-Cyano-11-(1-ethoxycarbonylmethyl-4-piperidylidene)-6,11-dihydro-5H-benzo[5,6]cyclohepta[1,2b]pyridine;

8-Cyano-11-(1-propoxycarbonylmethyl-4-piperidylidene)-6,11-dihydro-5H-benzo[5,6]cyclohepta[1,2b]pyridine;

8-Cyano-11-(1-methoxycarbonylethyl-4-piperidylidene)-6,11-dihydro-5H-benzo[5,6]cyclohepta[1,2b]pyridine;

8-Cyano-11-(1-ethoxycarbonylethyl-4-piperidylidene)-6,11-dihydro-5H-benzo[5,6]cyclohepta[1,2-b]pyridine;

8-Cyano-11-(1-propoxycarbonylethyl-4-piperidylidene)-6,11-dihydro-5H-benzo[5,6]cyclohepta[1,2b]pyridine;

8-Cyano-11-[1-(2-aminoethylcarbamoylmethyl)-4-piperidylidene]-6,11-dihydro-5H-benzo[5,6]cyclohepta[1,2-b]pyridine;

8-Cyano-11-[1-(3-aminopropylcarbamoylmethyl)-4-piperidylidene]-6,11-dihydro-5H-benzo[5,6]cyclohepta[1,2-b]pyridine;

8-Cyano-11-[1-(2-aminoethylcarbamoylethyl)-4piperidylidene]-6,11-dihydro-5H-benzo[5,6]cyclohepta[1,2-b]pyridine;

8-Cyano-11-[1-(3-aminopropylcarbamoylethyl)-4-piperidylidene]-6,11-dihydro-5H-benzo[5,6]cyclohepta[1,2-b]pyridine;

8-Methylsulfoxy-11-(1-methoxycarbonylmethyl-4-piperidylidene)-6,11-dihydro-5H-benzo[5,6]cyclohepta[1,2-b]pyridine;

8-Methylsulfoxy-11-[1-(2-aminoethylcarbamoylmethyl-4-piperidylidene]-6,11-dihydro-5H-benzo[5,6]cyclohepta[1,2-b]pyridine;

8-Methylsulfonyl-11-(1-methoxycarbonylmethyl-4-piperidylidene)-6,11-dihydro-5H-benzo[5,6]cyclohepta[1,2-b]pyridine;

8-Methylsulfonyl-11-[1-(2-aminoethylcarbamoylmethyl-4-piperidylidene]-6,11-dihydro-5H-benzo[5,6]cyclohepta[1,2-b]pyridine;

11-(1-Methoxycarbonylmethyl-4piperidylidene)-6,11-dihydro-5H-benzo[5,6]cyclohepta[1,2-b]pyridine-8-tetrazole;

11-[1-(2-Aminoethylcarbamoylmethyl-4-piperidylidene]-6,11-dihydro-5H-benzo[5,6]cyclohepta[1,2-b]pyridine-8-tetrazole;

11-(1-Methoxycarbonylmethyl-4-piperidylidene)-6,11-dihydro-5H-benzo[5,6]cyclohepta[1,2-b]pyridine-8-carboxamide;

11-[1-(2-Aminoethylcarbamoylmethyl-4-piperidylidene]-6,11-dihydro-5H-benzo[5,6]cyclohepta[1,2-b]pyridine -8-carboxamide;

11-(1-Methoxycarbonylmethyl-4-piperidylidene)-6,11-dihydro-5H-benzo[5,6]cyclohepta[1,2-b]pyridine-8-sulfonic acid; and 11-[1-(2-Aminoethylcarbamoylmethyl)-4-piperidylidene]-6,11-dihydro-5H-benzo[5,6]cyclohepta[1,2-b]pyridine-8-sulfonic acid.

A description will next be made of pharmacological effects of certain representative examples of the invention compounds (1) and their salts.

(1) Antihistaminergic action on the isolated guinea pig ileum

After a Hartley male guinea pig was sacrificed under ether anesthesia and exsanguination, the ileum was immediately isolated and a preparation was prepared. The preparation was suspended in a 20 ml Magnus bath containing 32° C. Tyrode solution (95% $O_2$–5% $CO_2$ saturation) and was placed under resting tension of 1 g. The isometrical changes of the muscular tension produced were recorded on the polygraph through the force displacement transducer. The preparation was allowed a minimal stabilization period of 30–60 minutes before undergoing experimentation and was observed the effect of each test compound on histamine ($10^{-5}$M)-induced contraction. $IC_{50}$ (M) value was determined graphically (dose-response curve) and represented the molar concentration of the test compound required to inhibit 50% of maximal response of histamine. The results are shown in Table 1.

TABLE 1

| Test compound | $IC_{50}$ (M) |
|---|---|
| Invention compound (Compound No. 1 obtained in Example 1) | $1.51 \times 10^{-8}$ |
| Comparative compound | |
| Terfenadine | $1.96 \times 10^{-7}$ |
| Loratadine | $1.23 \times 10^{-7}$ |

(2) Antiacetylcholinergic action on the isolated guinea pig ileum

The experiment was performed i a similar manner to experiment (1) except for the use of acetylcholine ($3 \times 10^{-5}$M) instead of histamine, so that the 50% inhibition concentration [$IC_{50}$ (M)] was determined. The results are shown in Table 2.

TABLE 2

| Test compound | $IC_{50}$ (M) |
|---|---|
| Invention compound (Compound No. 1 obtained in Example 1) | $4.85 \times 10^{-5}$ |
| Comparative compound | |
| Terfenadine | $3.91 \times 10^{-6}$ |
| Loratadine | $2.34 \times 10^{-5}$ |

(3) Antihistamine selectivity

From the results of the above experiments (1) and (2), the antihistamine selectivity was determined in accordance with the following formula. The results are shown in Table 3.

Antihistamine selectivity =

$$\frac{\text{Antiacetylcholinergic action, } IC_{50} \text{ (M) (Table 2)}}{\text{Antihistaminergic action, } IC_{50} \text{ (M) (Table 1)}}$$

TABLE 3

| Test compound | Antihistamic selectivity |
|---|---|
| Invention compound (Compound No. 1 obtained in Example 1) | 3212 |
| Comparative compound | |
| Terfenadine | 20 |
| Loratadine | 190 |

From the results of Table 3, it is understood that the invention compound (1) has a great difference between antiacetylcholinergic action and antihistaminergic action and hence extremely high antihistamine selectivity.

(4) Effect on histamine-induced dermovascular penetration increase In a shaved dorsal skin of a guinea pig (5-week old), 0.1 ml (1 μg) of histamine was intradermally injected. At the same time, 1.4% Evans blue physiological saline was intravenously injected at the rate of 0.1 ml/100 g body weight. Thirty minutes later, the animal was sacrificed under exsanguination and was evaluated by square of the shortest and the longest diameters of the blue spot (histamine-injected site). Each test compound was orally administered 60 minutes before the injection of histamine. The results are shown in Table 4.

TABLE 4

| Test compound | $ID_{50}$ (mg/kg) |
|---|---|
| Invention compound (Compound No. 1 obtained in Example 1) | 0.012 |
| Comparative compound | |
| Terfenadine | 3.344 |
| Loratadine | 0.534 |

(5) Effects on sleeping time Animals used in groups were ddy male mice, each group consisting of ten mice. After fasted for 24 hours, they were orally administered with a test compound. Upon an elapsed time of 1 hour after the oral administration, pentobarbital (50 mg/kg) was intraperitoneally administered and the sleeping time was measured. Statistical evaluation was performed by one-way analysis of variance, followed by the Turkey test for multiple comparison. The results are shown in Table 5.

TABLE 5

| Test compound | Dosage | No. of mice | Sleeping time (min) |
|---|---|---|---|
| Control | — | 10 | 46.6 ± 3.8 |
| Invention compound (Compound No. 1 obtained in Example 1) | 10 mg/kg | 10 | 62.9 ± 5.8 |
| Comparative compound Loratadine | 10 mg/kg | 10 | 75.7 ± 5.8** |

**$p < 0.01$ relative to the control.

(6) Acute toxicity

The invention compound (Compound No. 1) was orally administered to ICR mice. $LD_{50}$ value was found to be 657 mg/kg.

Antiallergic agents containing one of the compounds (1) according to this invention or a salt thereof can be formulated into dosage forms, for example, into tablets, hard capsules, soft capsules, granules, powders, fine granules, pills, troches, ointments, suppositories, injections, suspensions, emulsions, transfusions or syrups in a manner known per se and can then be administered through an oral or parenteral route. Oral administration is particularly preferred.

To formulate them into various dosage forms suited for oral or parenteral administration, the formulation can be conducted using conventional non-toxic additives such as excipients, binders, lubricants, disintegrators or suppository bases. Further, other additives such as isotonicities, stabilizers, dispersants, antioxidants, colorants, corrigents or buffers can also be used as needed.

It is also possible to incorporate one or more other drugs useful for the intended treatment.

The compounds (1) of this invention and their salts can be orally or parenterally administered as described above. Their daily dosage may range from 0.02 mg/kg to 2 mg/kg for adults, which may preferably be administered in 1-3 portions. The dosage and the frequency of administration can be modified depending on the administration route and the condition of each patient.

The present invention will hereinafter be described by the following examples and comparative examples. It is, however, to be borne in mind that the present invention is by no means limited to or by them.

REFERENTIAL EXAMPLE 1

8-Cyano-5,6-dihydro-1H-benzo[5,6]cyclohepta[1,2-b]pyridin-11-one

8-Bromo-5,6-dihydro-1H-benzo[5,6]cyclohepta[1,2-copper cyanide and a catalytic amount of sodium cyanide. The resultant mixture was refluxed for 6 hours. While the reaction mixture was still hot, it was poured into a solution of 7.2 g of sodium cyanide in 100 ml of water. The mixture thus obtained was stirred for 15 minutes. The mixture was cooled and then extracted with ethyl acetate. The resulting extract was dried over anhydrous $Na_2SO_4$, followed by filtration. The filtrate was concentrated under reduced pressure. The residue was purified by chromatography on a silica gel column and, from relevant chloroform eluate fractions, 2.5 g of 8-cyano-5,6-dihydro-1H-benzo[5,6]cyclohepta[1,2-b]pyridin-11-one were obtained (yield: 65%).

$^1$H-NMR δ ppm($CDCl_3$); 3.08-3.44(4H,m), 7.44(1H,dd), 7.60-7.80(3H,m), 8.14(1H,d), 8.76(1H,dd).

REFERENTIAL EXAMPLE 2

8-Cyano-6,11-dihydro-11-(1-methyl-4-piperidyl)-5H-benzo[5,6]cyclohepta[1,2-b]pyridin-11-ol Into a tetrahydrofuran (THF) solution of a Grignard reagent prepared from 6.7 g of N-methyl-4-chloropiperidine and 1.2 g of magnesium, 4.68 g of 8-cyano5,6-dihydro-1H-benzo[5,6]cyclohepta[1,2-b]pyridin-11-one (the compound prepared in Referential Example 1) were added under ice cooling. After the resultant mixture was stirred for 3 hours at room temperature, a saturated aqueous solution of ammonium chloride was added, followed by stirring for 15 minutes. The reaction mixture was then extracted with chloroform. The Extract was dried over anhydrous $Na_2SO_4$ and then filtered. The filtrate so obtained was concentrated under reduced pressure. The residue was purified by chromatography on a silica gel column and, from relevant fractions eluted with chloroform:methanol (50:1), 3.1 g of 8-cyano-6,11-dihydro-11-(1-methyl-4-piperidyl)-5H-benzo[5,6]cyclohepta[1,2-b]pyridin-11-ol were obtained (yield: 47%).

$^1$H-NMR δ ppm($CDCl_3$); 0.6-1.2(1H,m), 1.4-1.92(4H,m), 2.16(3H,s), 2.56-3.80(8H,m), 7.12-7.60(4H,m), 8.26(1H,d), 8.40(1H,dd).

REFERENTIAL EXAMPLE 3

8-Methylthio-5,6-dihydro-1H-benzo[5.6]cyclohepta[1.2-b]pyridin-11-one

8-Chloro-5,6-dihydro-1H-benzo[5,6]cyclohepta[1,2-b]pyridin-11-one (3.5 g) was dissolved in 60 ml of dimethylformamide, followed by the addition of 13.4 g of a 15% aqueous solution of methyl mercaptan sodium salt. The resultant mixture was refluxed for 14 hours. The reaction mixture was cooled and then concentrated under reduced pressure. Water was added to the residue, followed by extraction with methylene chloride. The resulting extract was washed with a brine, dried over anhydrous $MgSO_4$ and then filtered. The filtrate was concentrated under reduced pressure. The residue was purified by chromatography on a silica gel column and relevant chloroform eluate fractions were concentrated. The residue was recrystallized from toluene, whereby 3.57 g of 8-methylthio-5,6-dihydro-1H-benzo[5,6]cyclohepta[1,2-b]pyridin-11-one were obtained (yield: 97%). 2.50(3H,s), 3.16(4H,s), 7.00–7.52(3H,m), 7.66(1H,dd), 8.12(1H,d), 8 72(1H,dd).

REFERENTIAL EXAMPLE 4

8-Methylthio-6,11-dihydro-11-(1-methyl-4-piperidyl)-5H-benzo5,6]cyclohepta[1,2-b]pyridin-11-ol Into a THF solution of a Grignard reagent prepared from 1 16 g of N-methyl-4-chloropiperidine and 0.22 g of magnesium, 2.0 g of 8-methylthio-5,6-dihydro-1H-benzo[5,6]cyclohepta[1,2-b]pyridin-11-one were added under ice cooling. After the resultant mixture was stirred for 1 hour, the reaction mixture was treated in a similar manner to Referential Example 2 so that 2.06 g of the target compound, 8-methylthio-6,11-dihydro-11-(1-methyl-4-piperidyl)-5H-benzo[5,6]cyclohepta[1,2-b]pyridin-11-ol, were obtained (yield: 74%). CI-MS m/z: 355(M+1)+.

REFERENTIAL EXAMPLE 5

8-Methylthio-11-(1-methyl-4-piperidylidene)-6,11-dihydro-5H-benzo[5,6]cyclohepta[1,2-b]pyridine Thionyl chloride (6 ml) was added to 1.03 g of 8-methylthio-6,11-dihydro-11-(1-methyl-4-piperidyl)-5H-benzo[5,6]cyclohepta[1,2-b]pyridin-11-ol and the resulting mixture was refluxed for 1 hour. After the completion of the reaction, the reaction mixture was added with a 10% sodium hydroxide solution and then extracted with chloroform. The resultant extract was dried over anhydrous $Na_2SO_4$ and then filtered. The filtrate was concentrated under reduced pressure. The residue was purified by chromatography on a silica gel column and, from relevant fractions eluted with chloroform:methanol (20:1), 0.6 g of 8-methylthio-11-(1-methyl-4-piperidylidene)-6,11-dihydro-5H-benzo[5,6]cyclohepta[1,2-b]pyridine was obtained (yield: 61%).

$^1$H-NMR δ ppm(CDCl$_3$); 1.80–3.60(18H,m), 7.00–7.60(5H,m), 8.42(1H,dd).

REFERENTIAL EXAMPLE 6

8-Methylsulfonyl-5.6-dihydro-1H-benzo[5,6]-cyclohepta[1,2-b]pyridin-11-one

8-Methylthio-5,6-dihydro-1H-benzo[5,6]cyclohepta[1,2-b]pyridin-11-one (2.0 g) was dissolved in 100 ml of chloroform, followed by the addition of 3.55 g of m-chloroperbenzoic acid. The resultant mixture was left over for 24 hours in a cool dark place. The reaction mixture was basified with a 10% sodium carbonate solution and then extracted with chloroform. The chloroform extract was washed with a 10% sodium carbonate solution and then with a brine. The chloroform solution was dried over anhydrous $MgSO_4$ and then filtered. The filtrate was concentrated under reduced pressure and the residue was recrystallized from ethanol, whereby 2.1 g of 8-methylsulfonyl-5,6-dihydro-1H-benzo[5,6]cyclohepta[1,2-b]pyridin-11-one were obtained (yield: 93%).

$^1$H-NMR δ ppm(CDCl$_3$); 3.08(3H,s), 3.16–3.48(3H,m), 7.32–7.56(1H,m), 7.64–7.80(1H,dd), 7.80–8.00(2H,m), 8.08–8.24(1H,d), 8.64–8.84(1H,dd).

REFERENTIAL EXAMPLE 7

8-Methylsulfonyl-6,11-dihydro-11-(1-methyl-4-piperidyl)-5H-benzo[5,6]cyclohepta[1,2-b]pyridin-11-ol 8-Methylsulfonyl-5,6-dihydro-1H-benzo[5,6]cyclohepta[1,2-b]pyridin-11-one (1 g) was dissolved in 30 ml of methylene chloride, followed by the dropwise gradual addition of a Grignard reagent under ice cooling. The Grignard reagent had been prepared from 0.07 g of N-methyl-4-chloropiperidine, 0.012 g of magnesium and 10 ml of THF. After the resultant mixture was stirred for 1 hour at the same temperature, it was stirred for additional 1 hour at room temperature. The reaction mixture was then treated in a similar manner to Referential Example 2, whereby 0.82 g of the target compound, 8-methylsulfonyl-6,11-dihydro-11-(1-methyl-4-piperidyl)-5H-benzo[5,6]cyclohepta[1,2-b]pyridin-11-ol was obtained (yield: 61%).

MS m/z: 386(M+).

EXAMPLE 1

8-Cyano-11-(1-methyl-4-piperidylidene)-6,11-dihydro-5H-benzo[5,6]-cyclohepta[1,2-b]pyridine (Compound No. 1)

Thionyl chloride (15 ml) was added to 2.7 g of 8-cyano-6,11-dihydro-11-(1-methyl-4-piperidyl)-5H-benzo[ 5,6]cyclohepta[1,2-b]pyridin-11-ol, followed by reflux for 8 hours. The reaction mixture was concentrated under reduced pressure. An aqueous solution of sodium hydroxide was added to the residue to render the latter basic, followed by extraction with chloroform. The extract was dried over anhydrous $Na_2SO_4$ and filtered and the filtrate was concentrated under reduced pressure. The residue was purified by chromatography on a silica gel column and, from relevant fractions eluted with chloroform:methanol (50:1), 1.6 g of 8-cyano-11-(1-methyl-4-piperidylidene)-6,11-dihydro-5H-benzo[5,6]cyclohepta[1,2-b]pyridine were obtained (yield: 63%).

EXAMPLE 2

11-(1-Methyl-4-piperidylidene)-6,11-dihydro-5H-benzo[5,6]cyclohepta[1.2-b]pyridine-8-carboxamide (Compound No. 2)

Ethanol (150 ml) was added to 2 g of 8-cyano-11-(1-methyl-4-piperidylidene)-6,11-dihydro-5H-benzo[5,6-]cyclohepta[1,2-b]pyridine so that the latter was dissolved in the former. An aqueous solution of 2.8 g of potassium hydroxide was added further, followed by reflux for 3.5 hours. After the reaction, the solvent was distilled off under reduced pressure and a brine was added to the residue, followed by extraction with chloroform. The extract was dried over anhydrous $Na_2SO_4$ and then filtered. The filtrate was concentrated under reduced pressure. The residue was purified by chromatography on a silica gel column and, from relevant fractions eluted with chloroform:methanol 25:1 and 10:1), 1.4 g of 11-(1-methyl-4-piperidylidene)-6,11-dihydro-5H-benzo[5,6]cyclohepta[1,2-b]pyridine-8-carboxamide were obtained (yield: 66%).

EXAMPLE 3

8-Methylsulfoxy-11-(1-methyl-4-piperidylidene)-6,11-dihydro-5H-benzo[5,6]cyclohepta[1,2-b]pyridine (Compound No. 3)

8-Methylthio-11-(1-methyl-4-piperidylidene)-6,11-dihydro-5H-benzo[5,6]cyclohepta[1,2-b]pyridine (0.3 g) was dissolved in 20 ml of methanol, which 20 ml of an aqueous solution containing 0.52 g of $NaBrO_2 \cdot 3H_2O$ were added dropwise under stirring at room temperature. After the reaction mixture was stirred for 3 hours at the same temperature, the solvent was distilled off and water was added to the residue, followed by extraction with methylene chloride. The extract was washed with a 10% sodium hydroxide solution, dried over anhydrous $Na_2SO_4$ and then filtered. The filtrate was concentrated under reduced pressure. The residue was purified by column chromatography and, from relevant fractions eluted with chloroform:methanol (20:1), 0.12 g of 8-methylsulfoxy-11-(1-methyl-4-piperidylidene)-6,11-dihydro-5H-benzo[5,6]cyclohepta[1,2-b]pyridine was obtained (yield: 36%).

EXAMPLE 4

8-Methylsulfonyl-11-(1-methyl-4-piperidylidene)-6,11-dihydro-5H-benzo[5,6]cyclohepta[1,2-b]pyridine (Compound No. 4)

To 1.35 g of 8-methylsulfonyl-6,11-dihydro-11-(1-methyl-4-piperidyl)-5H-benzo[5,6]cyclohepta[1,2-b]pyridin-11-ol, 24 ml of a mixed solution of conc. $H_2SO_4$ and $CF_3SO_3H$ (2:1) were added. The resultant mixture was stirred at 50° C. for 5 hours. After the reaction, the reaction mixture was poured into ice water, basified with a 20% sodium hydroxide solution and then extracted with methylene chloride. The extract was washed with a saturated aqueous solution of sodium chloride, dried over anhydrous $MgSO_4$ and then filtered. The filtrate was concentrated under reduced pressure. The residue was purified by chromatography on an alumina column, whereby 0.95 g of 8-methylsulfonyl-11-(1-methyl-4-piperidylidene)-6,11-dihydro-5H-benzo]5,6]cyclohepta[1,2-b]pyridine was obtained (yield: 74%).

EXAMPLE 5

8-Cyano-11-(1-ethoxycarbonyl-4-piperidylidene)-6,11-dihydro-5H-benzo[5,6]cyclohepta[1,2-b]pyridine (Compound No. 5)

Toluene (40 ml) was added to 1 g of 8-cyano-11-(1-methyl-4-piperidylidene)-6,11-dihydro-5H-benzo[5,6-]cyclohepta[1,2-b]pyridine to dissolve the latter, followed by the addition of 0.52 g of triethylamine and 1.92 g of ethyl chloroformate. The resulting mixture was refluxed for 2.5 hours. The mixture was cooled and washed with water. The organic layer was dried over anhydrous $Na_2SO_4$ and then filtered. The filtrate was concentrated under reduced pressure. The residue was purified by chromatography on a silica gel column. The substance eluted with chloroform was recrystallized from n-hexane, whereby 0.89 g of 8-cyano-11-(1-ethoxycarbonyl-4-piperidylidene)-6,11-dihydro-5H-benzo[5,6]cyclohepta[1,2-b]pyridine was obtained (yield: 75%).

EXAMPLE 6

8-Cyano-11-[1-(2,2,2-trichloroethoxycarbonyl)-4-piperidylidene]-6,11-dihydro-5H-benzo[5,6]cyclohepta[1,2-b]pyridine (Compound No. 6)

Toluene (40 ml) was added to 0.64 g of 8-cyano-11-(1-methyl-4-peridylidene)-6,11-dihydro-5H-benzo[ 5,6]cyclohepta[1,2-b]pyridine. The resultant solution was added with 0.21 g of triethylamine and 0.86 g of 2,2,2-trichloroethyl chloroformate, followed by reflux for 5 hours. The reaction mixture was then treated in a similar manner to Example 5, whereby 0.71 g of 8-cyano-11-[1-(2,2,2-trichloroethoxycarbonyl)-4-piperidylidene]-6,11-dihydro-5H-benzo[5,6]cyclohepta[1,2-b]pyridine was obtained (yield: 73%).

EXAMPLE 7

8-Cyano-11-(4-piperidylidene)-6,11-dihydro-5H-benzo[5.6]cyclohepta[1,2-b]pyridine (Compound No. 7)

Acetic acid (25 ml) was added to 1 g of 8-cyano-11-[1-(2,2,2-trichloroethoxycarbonyl)-4-piperidylidene]-6,11-dihydro-5H-benzo[5,6]cyclohepta[1,2-b]pyridine to dissolve the latter, followed by the addition of 2.75 g of zinc powder. The resulting mixture was heated under stirring for 2.5 hours over an oil bath of 70°-80° C. After the reaction, the reaction mixture was basified with a sodium hydroxide solution and then extracted with chloroform. The extract was dried over anhydrous $Na_2SO_4$ and then filtered. The filtrate was concentrated under reduced pressure and the residue was purified by chromatography on a silica gel column. From relevant fractions eluted with chloroform:methanol (10:1), 0.41 g of 8-cyano-11-(4-piperidylidene)-6,11-dihydro-5H-benzo[5.6]cyclohepta[1,2-b]pyridine was obtained (yield: 65%).

EXAMPLE 8

8-Cyano-11-(1-acetyl-4-piperidylidene)-6,11-dihydro-5H-benzo[5,6]cyclohepta[1,2-b]pyridine (Compound No. 8)

Pyridine (4 ml) was added to 0.4 g of 8-cyano-11-(4-piperidylidene)-6,11-dihydro-5H-benzo[5,6]cyclohepta[1,2-b]pyridine to dissolve the latter, followed by the addition of 8 ml of acetic anhydride. At the room temperature, the resulting mixture was stirred for 4 hours. After the completion of the reaction, the reaction mixture was concentrated under reduced pressure. Water was added to the residue, followed by extraction with chloroform. The extract was next dried over anhydrous $Na_2SO_4$ and the chloroform was distilled off under reduced pressure. The residue was purified by chromatography on a silica gel column and, from relevant fractions eluted with chloroform:methanol (100:1), 0.3 g of 8-cyano-11-(1-acetyl-4-piperidylidene)-6,11-dihydro-5H-benzo[5,6]cyclohepta[1,2-b]pyridine was obtained (yield: 66%).

EXAMPLE 9

8-Cyano-11-(1-benzoyl-4-piperidylidene)-6,11-dihydro-5H-benzo[5,6]cyclohepta[1,2-b]pyridine (Compound No. 9)

Dry THF (20 ml) was added to 0.4 g of 8-cyano-1-(4-piperidylidene)-6,11-dihydro-5H-benzo[5,6]cyclohepta[1,2-b]pyridine to dissolve the latter, followed by the addition of 0.2 g of triethylamine and 0.2 g of benzoyl chloride. The resultant mixture was stirred at room temperature for 4 hours. After the completion of the reaction, water was added and the resulting mixture was extracted with chloroform. The extract was dried over anhydrous Na₂SO₄. The chloroform was distilled off under reduced pressure. The residue was purified by chromatography on a silica gel column and, from relevant fractions eluted with chloroform:methanol (100:1), 0.34 g of 8-cyano-11-(1-benzoyl-4-piperidylidene)-6,11-dihydro-5H-benzo[5,6]cyclohepta[1,2-b]pyridine was obtained (yield: 63%).

EXAMPLE 10

8-Cyano-11-(1-N,N-dimethylaminocarbonyl-4-piperidylidene)-6,11-dihydro-5H-benzo[5,6]cyclohepta[1,2-b]pyridine (Compound No. 10)

Dry THF (30 ml) was added to 0.44 g of 8-cyano-11-(4-piperidylidene)-6,11-dihydro-5H-benzo[5,6]cyclohepta[1,2-b]pyridine to dissolve the latter, followed by the addition of 0.3 g of triethylamine and 0.24 g of N,N-dimethylcarbamoyl chloride. The resultant mixture was stirred at room temperature for 4 hours. The reaction mixture was then treated in a similar manner to Example 9, whereby 0.34 g of the target compound, 8-cyano-11-(1-N,N-dimethylaminocarbonyl-4-piperidylidene)-6,11-dihydro-5H-benzo[5,6]cyclohepta[1,2-b]pyridine was obtained (yield: 63%).

EXAMPLE 11

8-Cyano-11-(1-ethoxycarbonylmethyl-4-piperidylidene-6,11-dihydro-5H-benzo[5,6]cyclohepta[1,2-b]pyridine (Compound 11)

Dry THF (20 ml) was added to 0.4 g of 8-cyano-11-(4-piperidylidene)-6,11-dihydro-5H-benzo[5,6]cyclohepta[1,2-b]pyridine to dissolve the latter, followed by the addition of 0.2 g of triethylamine and 0.27 g of ethyl bromoacetate. The resultant mixture was stirred at room temperature for 24 hours. After the completion of the reaction, THF was distilled off under reduced pressure, the residue was dissolved in chloroform, and the resultant solution was washed with water. The chloroform layer was dried over anhydrous Na₂SO₄ and then filtered. The chloroform was distilled off under reduced pressure. The residue was purified by chromatography on a silica gel column and, from relevant fractions eluted with chloroform:methanol (20:1), 0.5 g of 8-cyano-11-(1-ethoxycarbonylmethyl-4-piperidylidene)-6,11-dihydro-5H-benzo[5,6]cyclohepta[1,2-b]pyridine was obtained (yield: 97%).

EXAMPLE 12

8-Cyano-11-[1-(2-aminoethylcarbamoylmethyl)-4-piperidylidene]-6.11-dihydro-5H-benzo[5,6]cyclohepta[1,2-b]pyridine (Compound No. 12)

Ethylenediamine (4 ml) was added to 0.5 g of 8-cyano-11-(1-ethoxycarbonylmethyl-4-piperidylidene)6,11-dihydro-5H-benzo[5,6]-cyclohepta[1,2-b]pyridine, followed by stirring at 70°-80° C. for 3 hours. After the reaction, water was added and the resulting mixture was extracted with ethyl acetate. The extract was dried over anhydrous Na₂SO₄. The ethyl acetate was distilled off under reduced pressure. The residue was purified by chromatography on a silica gel column and, from relevant fractions eluted with chloroform:methanol (20:1 - 10:1), 0.32 g of 8-cyano-11-[1-(2-aminoethylcarbamoylmethyl)-4-piperidylidene]-6,11-dihydro-5H-benzo[5,6]cyclohepta[1,2-b]pyridine was obtained (yield: 62%).

Data of Compound Nos. 1-12 obtained above in Examples 1-12 are summarized in Table 6.

TABLE 6

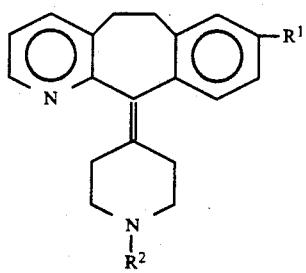

| Comp'd No. | Formula (1) R¹ | R² | Appearance mp (°C.) | NMR (CDCl₃, δ ppm) |
|---|---|---|---|---|
| 1 | —CN | —CH₃ | 163-164 | 1.68-3.68(15H, m), 7.00-7.60(5H, m), 8.44(1H, dd) |
| 2 | —CONH₂ | —CH₃ | 239-241.5 | 1.96-3.04(10H, m), 2.28(3H, s), 3.24-3.60(2H, m) 6.0(2H, br), 7.04-7.80(5H, m), 8.48(1H, dd) |
| 3 | —SOCH₃ | —CH₃ | Pale red syrup | 1.60-3.80(18H, m), 7.00-7.28(1H, m), 7.28-7.72(4H, m), 8.32-8.56(1H, m) |
| 4 | —SO₂CH₃ | —CH₃ | Pale yellowish brown powder | 1.80-3.80(18H, m), 7.00-7.24(1H, m), 7.32-7.56(2H, m), 7.60-7.84(2H, m), 8.36-8.52(1H, m) |
| 5 | —CN | —COOC₂H₅ | 154-156 | 1.30(3H, t), 2.20-3.96(12H, m), 4.16(2H, q), 7.08-7.62 (5H, m), 8.48(1H, dd) |
| 6 | —CN | —COOCH₂CCl₃ | Colorless syrup | 2.20-4.08(12H, m), 4.76(2H, s), 7.00-7.64(5H, m), 8.50(1H, dd) |
| 7 | —CN | —H | 203-207 | 2.20-3.60(12H, m), 6.98-7.60(5H, m), 8.48(1H, dd) |
| 8 | —CN | —COCH₃ | Colorless crystals (99-102.5° C.) | 2.08(3H, s), 2.20-4.24(12H, m), 7.08-7.60(5H, m) |
| 9 | —CN | —COC₆H₅ | Colorless crystals (110-113.5° C.) | 1.60-3.60(12H, m), 7.00-7.60(10H, m), 8.40(1H, dd) |
| 10 | —CN | —CON(Me)(Me) | Colorless crystals (180-182° C.) | 2.24-3.72(12H, m), 2.80(6H, s), 7.08-7.60(5H, m), 8.48(1H, dd) |
| 11 | —CN | —CH₂COOC₂H₅ | Yellow oil | 2.28(3H, t), 2.08-3.60(14H, m), 4.20(2H, q), |

TABLE 6-continued

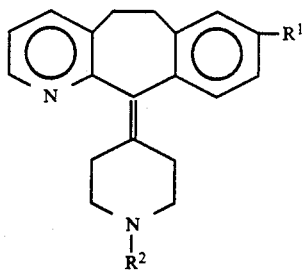

| Comp'd No. | Formula (1) R$^1$ | R$^2$ | Appearance mp (°C.) | NMR (CDCl$_3$, δ ppm) |
|---|---|---|---|---|
| 12 | —CN | —CH$_2$CONH(CH$_2$)$_2$NH$_2$ | Yellow oil | 7.04–7.60(5H, m), 8.48(1H, dd) 1.64(3H, br.s), 2.04–3.60(18H, m), 7.08–7.60(5H, m), 8.48(1H, dd) |

A description will next be made as to specific examples of preparations containing Compound No. 1 of the present invention.

| Preparation Example 1 Tablets | |
|---|---|
| Basis (Compound No. 1) | 5 mg |
| Crystalline cellulose | 45 mg |
| Lactose | 37.5 mg |
| Hydroxypropylcellulose | 1 mg |
| Talc | 1 mg |
| Magnesium stearate | 0.5 mg |
| Total | 90 mg |

The above ingredients were weighed in the above amount, respectively, and were thoroughly mixed together. The resultant mixture was compressed in a manner known per se in the art so that tablets were obtained. The tablets so obtained can be treated further into sugar coated tablets or film coated tablets as needed.

| Preparation Example 2 Capsules | |
|---|---|
| Basis (Compound No. 1) | 5 mg |
| Corn starch | 20 mg |
| Lactose | 110.8 mg |
| Light anhydrous silicic acid | 0.2 mg |
| Talc | 4 mg |
| Total | 140 mg |

The above ingredients in the respective amounts were thoroughly mixed and then filled in No. 4 capsules.

| Preparation Example 3 Granule | |
|---|---|
| Basis (Compound No. 1) | 5 mg |
| Corn starch | 100 mg |
| Calcium carboxymethylcellulose | 50 mg |
| Refined sucrose | 845 mg |
| Total | 1,000 mg |

The above ingredients were weighed in the above amounts, respectively, and then formulated into a granule in a manner known per se in the art.

| Preparation Example 4 Ointment | |
|---|---|
| Basis (Compound No. 1) | 0.05 g |
| Propylene glycol | 10 g |
| Sorbitan sesquioleate | 3 g |
| White petrolatum | q.s. to 100 g |

The above ingredients were weighed in the above amounts, respectively, and then formulated into an ointment in a manner known per se in the art.

| Preparation Example 5 Injection | |
|---|---|
| Basis (Compound No. 1) | 2 mg |
| Sodium dihydrogenphosphate | 5 mg |
| Sodium chloride | 10 mg |
| Injection-grade, distilled water | q.s. to 2 mM |

The above ingredients were measured in the above amounts, respectively, and then formulated into an injection in a manner known per se in the art.

| Preparation Example 6 Syrup | |
|---|---|
| Basic (Compound No. 1) | 0.01 g |
| Sucrose | 50 g |
| Citric acid | 0.1 g |
| Butyl paraoxybenzoate | 0.014 g |
| Sodium hydroxide | as needed |
| distilled water | q.s. to 100 ml |

The above ingredients were measured in the above amounts, respectively, and then formulated into a syrup in a manner known per se in the art.

| Preparation Example 7 Suppository | |
|---|---|
| Basis (Compound No. 1) | 3 mg |
| Hard fat | q.s. to 1,200 mg |

The above ingredients were weighed in the above amounts, respectively, and then formulated into a suppository in a manner known per se in the art.

| Preparation Example 8 | |
|---|---|
| Cream | |
| Basis (Compound No. 1) | 0.05 g |
| Cetanol | 4 g |
| White petrolatum | 8 g |
| Light liquid paraffin | 5 g |
| Glycerin monostearate | 3 g |
| Polyoxyethylene cetyl ether | 1.5 g |
| Propylene glycol | 10 g |
| Butyl paraoxybenzoate | 0.1 g |
| Methyl paraoxybenzoate | 0.2 g |
| Purified water | q.s. to 100 g |

The above ingredients were weighed in the above amounts, respectively, and then formulated into a cream in a manner known per se in the art.

We claim:

1. A benzo[5,6]cyclohepta[1,2-b]pyridine derivative having the following formula (1):

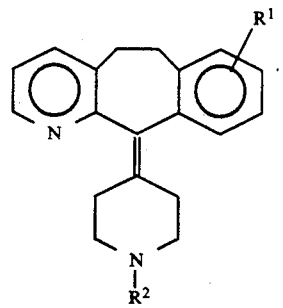

wherein $R^1$ is a cyano, carbamoyl, tetrazolyl or sulfonic acid group; and $R^2$ is a hydrogen atom, a cyano, phenyl, phenylalkyl, alkoxycarbonylalkyl, aminoalkylcarbamoylalkyl or lower alkyl group, a

group wherein X is an oxygen or sulfur atom and $R^3$ is a hydrogen atom, a lower alkyl group which may be substituted by one or more halogen atoms or lower alkoxy groups, an alkylamino group, or a substituted or unsubstituted phenyl or phenylalkyl group, or a —X—$R^4$ group wherein X is an oxygen or sulfur atom and $R^4$ is a lower alkyl group which may be substituted by one or more halogen atoms, a substituted or unsubstituted phenyl or phenylalkyl group, or an aminoalkyl group; or a salt thereof.

2. An antiallergic agent comprising an effective amount of the benzo[5,6]cyclohepta[1,2-]pyridine derivative having formula (1) or salt thereof according to claim 1 and a pharmaceutically acceptable carrier.

3. An antihistamic agent comprising an effective amount of the benzo[5,6]cyclohepta[1,2-b]pyridine derivative having formula (1) or salt thereof according to claim 1 and a pharmaceutically acceptable carrier.

* * * * *

UNITED STATES PATENT AND TRADEMARK OFFICE
CERTIFICATE OF CORRECTION

Page 1 of 5

PATENT NO. : 5,231,101
DATED : July 27, 1993
INVENTOR(S) : Haruyoshi Honda, et. al.

It is certified that error appears in the above-indentified patent and that said Letters Patent is hereby corrected as shown below:

TITLE PAGE, Under [57], Line 36, ABSTRACT, "-X-R₄" should read -- -X-R⁴--.

COLUMN 1, TITLE "[1,2-B]" should read --[1,2-b]--.

COLUMN 2, LINE 58, "R²R³" should read --R²,R³--.

COLUMN 11, LINE 47, "methylamionothiocarbonyl" should read --methylaminothiocarbonyl--;

LINE 51, "piperidylidene)" should read -- piperidylidene]--.

COLUMN 12, LINE 21 "[5,6]1,2-" should -- [5,6]cyclohepta[1,2- --;

LINE 43, "8tetrazole;" should read --8-tetrazole;--;

LINE 51, "8carboxa-" should read --8-carboxa- --.

COLUMN 13, LINE 2, "pyridine-8car-" should read -- pyridine-8-car- --;

LINE 6, "8carboxamide;" should read --8-carboxamide;--;

LINE 29, "pyridine-8sul-" should read --pyridine-8-sul- --;

UNITED STATES PATENT AND TRADEMARK OFFICE
CERTIFICATE OF CORRECTION

PATENT NO. : 5,231,101
DATED : July 27, 1993
INVENTOR(S) : Haruyoshi Honda, et. al.

It is certified that error appears in the above-indentified patent and that said Letters Patent is hereby corrected as shown below:

COLUMN 13, LINE 36, "pyridine-8sul-" should read -- pyridine- 8-sul- --;

LINE 40, "8sulfonic" should read --8-sulfonic--;

LINE 45, "piperidylidene]6,11-" should read -- piperidylidene]-6,11- --.

COLUMN 14, LINE 54, "-8carboxa-" should read -- -8-carboxa- --;

LINE 58, "piperidylidene)6,11-" should read -- piperidylidene)-6,11- --;

LINE 60, "piperidylidene)6,11-" should read -- piperidylidene)-6,11- --.

COLUMN 15, LINE 27, "(3-dimethoxybenzoyl" should read --(3,4-dimethoxybenzoyl--;

LINE 33, "-11(1-" should read -- -11-(1- --;

LINE 38, "-11(1-" should read -- -11-(1- --;

LINE 46, "[1,2b]pyri-" should read --[1,2-b]pyri- --;

LINE 64, ")6,11-" should read --)-6,11- --;

LINE 67, "[1,2b]pyri-" should read --[1,2-b]pyri- --.

COLUMN 16, LINE 2, "[1,2b]pyri-" should read --[1,2-b]pyri- --;

UNITED STATES PATENT AND TRADEMARK OFFICE
CERTIFICATE OF CORRECTION

PATENT NO. : 5,231,101
DATED : July 27, 1993
INVENTOR(S) : Haruyoshi Honda, et. al.

It is certified that error appears in the above-indentified patent and that said Letters Patent is hereby corrected as shown below:

COLUMN 16, LINE 9, "(11-methoxyacetyl" should read --(1-methoxyacetyl--;

LINE 13, "[1,2b]pyri- should read --[1,2-b]pyri- --;

LINE 19, ")   -5H-benzo" should read --)-6,11-dihydro-5H-benzo--;

LINE 32, "-8sulfonic" should read -- -8-sulfonic--;

LINE 54, "-8tetrazole" should read -- -8-tetrazole --;

LINE 55, "1-(1-Aminoacetyl" should read --11-(1-Aminoacetyl--;

LINE 67, "-11-(1-cyano-4-" should read -- -(1-formyl-4- --.

COLUMN 17, LINE 3, , "[1,2b]" should read --[1,2-b];

LINE 6, "[1,2b]" should read --[1,2-b]--;

LINE 9, "[1,2b]" should read --[1,2-b]--;

LINE 12, "[1,2b]" should read --[1,2-b]--;

LINE 26, "4piperidylidene" should read --4-piperidylidene--;

LINE 43, "-4piperidylidene)" should read -- -4-piperidylidene)--.

UNITED STATES PATENT AND TRADEMARK OFFICE
CERTIFICATE OF CORRECTION

PATENT NO. : 5,231,101
DATED : July 27, 1993
INVENTOR(S) : Haruyoshi Honda, et. al.

It is certified that error appears in the above-indentified patent and that said Letters Patent is hereby corrected as shown below:

COLUMN 18, LINE 2, "32°C. Tyrode" should read --32°C Tyrode--;

LINE 27, "i a similar" should read --in a similar--;

LINE 67, "tion increase In a shaved...." should read

--tion increase.
          In a shaved......--.

COLUMN 19, LINE 20, "(5)Effects...time Animals..." should read
    --(5)Effects...time.
       Animals...--.

COLUMN 20, between Lines 12 and 13, please insert --b]pyridin-11-one (4.75 g) was dissolved in 100 ml ofdimethylformamide, followed by the addition of 3.7 g of--;

LINE 35, "cyano5,6-dihydro" should read --cyano-5,6-dihydro--;

LINE 57, "ta[1,2-b]pyridin" should read --ta[1,2-b]pyridin--.

COLUMN 21, LINE 6, "...97%).2.50(..." should read
--...97%).
$^1$H-NMR δ ppm(CDCl$_3$); 2.50(...--;

LINE 12, "benzo5,6]" should read --benzo[5,6]--.

UNITED STATES PATENT AND TRADEMARK OFFICE
CERTIFICATE OF CORRECTION

PATENT NO. : 5,231,101
DATED : July 27, 1993
INVENTOR(S) : Haruyoshi Honda, et. al.

It is certified that error appears in the above-indentified patent and that said Letters Patent is hereby corrected as shown below:

COLUMN 23, LINE 50, "-6.11-" should read -- -6,11- --.

COLUMN 24, LINE 35, "zo[5.6]cyclohepta" should read -- zo[5,6]cyclohepta--;

LINE 64, "cyano-1-(4-" should read --cyano-11-(4- --.

COLUMN 27, LINE 37, "amount, respectively," should read -- amounts, respectively,--.

COLUMN 28, LINE 50, "Basic(Compound No.1)" should read -- Basis(Compound No.1)--.

COLUMN 30, LINE 20, "$-C-R^3$" should read -- $-C-R^3$ --;
$\phantom{-C-}\|$ $\phantom{\text{should read -- }-C-}\|$
$\phantom{-C-}X$ $\phantom{\text{should read -- }-C-}X$ LINE 28, "$-X-^4$" should read -- $-X-R^4$--.

LINE 35, "[1,2-]pyridine" should read --[1,2-b]pyridine--.

Signed and Sealed this

Third Day of January, 1995

BRUCE LEHMAN

Attest:

Attesting Officer

Commissioner of Patents and Trademarks